(12) United States Patent
Moehring et al.

(10) Patent No.: US 12,390,184 B2
(45) Date of Patent: Aug. 19, 2025

(54) WEARABLE AUSCULTATION DEVICE

(71) Applicant: OtoNexus Medical Technologies, Inc., Bellevue, WA (US)

(72) Inventors: Mark A. Moehring, Seattle, WA (US); Anthony J. Alleman, Snohomish, WA (US)

(73) Assignee: OtoNexus Medical Technologies, Inc., Bellevue, WA (US)

( * ) Notice: Subject to any disclaimer, the term of this patent is extended or adjusted under 35 U.S.C. 154(b) by 0 days.

(21) Appl. No.: 18/171,215

(22) Filed: Feb. 17, 2023

(65) Prior Publication Data

US 2023/0190222 A1  Jun. 22, 2023

Related U.S. Application Data

(63) Continuation of application No. PCT/US2021/046754, filed on Aug. 19, 2021.

(60) Provisional application No. 63/067,502, filed on Aug. 19, 2020.

(51) Int. Cl.
  *A61B 7/04*  (2006.01)
  *A61B 5/0205*  (2006.01)
  *A61B 7/00*  (2006.01)

(52) U.S. Cl.
  CPC .............. *A61B 7/04* (2013.01); *A61B 5/0205* (2013.01); *A61B 7/003* (2013.01)

(58) Field of Classification Search
  CPC .... A61B 5/08; A61B 5/24; A61B 7/00; A61B 7/04; A61B 7/003; A61B 5/0205; A61B 5/0048; A61B 5/0053; A61N 1/365; A63B 24/00

USPC .......................................................... 600/586
See application file for complete search history.

(56) References Cited

U.S. PATENT DOCUMENTS

| | | | |
|---|---|---|---|
| 7,976,480 B2* | 7/2011 | Grajales | A61B 5/6804 600/528 |
| 8,394,031 B2* | 3/2013 | Mansy | A61B 7/04 600/550 |
| 8,827,920 B2* | 9/2014 | Lee | A61B 5/742 600/528 |
| 2011/0009759 A1* | 1/2011 | Rajamani | A61B 5/6805 600/526 |
| 2013/0169111 A1* | 7/2013 | Ibata | G01S 7/521 310/322 |
| 2013/0226019 A1 | 8/2013 | Pretorius et al. | |
| 2017/0209115 A1* | 7/2017 | Lönnroth | A61B 5/11 |

(Continued)

FOREIGN PATENT DOCUMENTS

CN  1870941 A  11/2006

OTHER PUBLICATIONS

PCT/US2021/046754 International Search Report and Written Opinion dated Nov. 29, 2021.

(Continued)

*Primary Examiner* — Devin B Henson
(74) *Attorney, Agent, or Firm* — Wilson Sonsini Goodrich & Rosati (57) ABSTRACT

Provided herein are systems, devices, and methods to measure auditory signals from a subject to determine a state of a subject. The auditory signals measured may provide a tool to monitor the development of disease state(s) or abnormal physiologic conditions (e.g., wheezing, fluid accumulation, abnormal heart murmur or rhythm, etc).

32 Claims, 3 Drawing Sheets

(56) References Cited

U.S. PATENT DOCUMENTS

| | | | |
|---|---|---|---|
| 2018/0132815 A1* | 5/2018 | Tsai | A61B 5/42 |
| 2018/0367921 A1* | 12/2018 | Murarka | H04R 25/505 |
| 2019/0099152 A1 | 4/2019 | Martin et al. | |
| 2019/0142686 A1* | 5/2019 | Lee | A61H 31/00 |
| | | | 601/44 |
| 2019/0357777 A1 | 11/2019 | LeBoeuf et al. | |
| 2020/0107800 A1* | 4/2020 | Nieminen | A61B 5/7203 |
| 2020/0178923 A1 | 6/2020 | Telfort et al. | |
| 2023/0226293 A1* | 7/2023 | Ashkenazi | A61H 9/0078 |
| | | | 128/204.21 |

OTHER PUBLICATIONS

Visagie, et al., Autonomous detection of heart sound abnormalities using an auscultation jacket. Australasian Physical & Engineering in Medicine vol. 32 No. 4, 2009. pp. 240-250. DOI: 10.1007/bf03179245.

\* cited by examiner

302
Detect one or more auditory signals from a subject using one or more air coupled auscultation modules

↓

304
Process the one or more auditory signals to determine a correlative relationship between the one or more auditory signals from the subject and a library of one or more auditory signals

↓

306
Determine a physiologic state of the subject based on the correlative relationship between the one or more auditory signals

FIG. 3

WEARABLE AUSCULTATION DEVICE

CROSS-REFERENCE

This application is a continuation of PCT Application No. PCT/US21/46754, filed Aug. 19, 2021, which claims the benefit of U.S. Provisional Application No. 63/067,502 filed Aug. 19, 2020, the entire contents of which are incorporated herein by reference.

BACKGROUND

Traditional auscultation utilizes a stethoscope to observe auditory signals emitted from biological systems, e.g., the human lungs, gastro-intestinal track, heart, etc., indicative of a state of health for a subject. Unfortunately, due to the typical single point measurement nature of auscultation, spatial information of where such a signal originates from can be lost. Additionally, the cumbersome nature of typical auscultation achieved by a stethoscope limits the application of such a technique to specialized physician interpretation providing a single measurement in time. Therefore, there exists unmet needs for a platform capable of continual auscultation to determine a change in the state of health of a subject.

SUMMARY

The present disclosure provides devices, systems, and methods to measure auditory signals emitted by a subject. In some cases, the disclosure describes one or more auscultation modules positioned around a subject, each capable of independently measuring auditory signals at a discrete surface on the subject. The one or more auscultation modules positioned around the subject may comprise a unique spatial address that in combination with gyroscopic and accelerometer information may provide 3-D spatial localization of detected auditory signals.

The present disclosure addresses the aforementioned unmet needs by automating and multiplexing the measurement of auditory signals of a subject. The present disclosure, in some cases, provides an array of auscultation modules positioned around a subject with a known spacing and angular displacement such that the spatial position of an auditory signal may be calculated between the measured auditory signals between each of the one or more auscultation modules. Additionally, the present disclosure provides a processor and/or computational system configured to interpret and classify the auditory signals, removing subjective interpretation by a physician and enabling the wider use of a platform in circumstances where an expert interpreter (e.g., physician, respiratory therapist, etc) is unavailable. Lastly, the devices and systems of the disclosure described herein may be fastened or otherwise worn by the subject in a non-obtrusive manner enabling, in some embodiments, continual monitoring of auditory signals. Such continuous monitoring of auditory signals and the non-obtrusive nature of the device provides the unexpected result of determining early changes in a subjects anatomy or physiology that may be correlated and/or associated to development or changes in a disease state.

In some aspects, the disclosure provided herein, in some embodiments, describes a device to measure biological auditory signals, the device comprises: a wearable housing; one or more transducers coupled to the wearable housing configured to receive one or more auditory signals from a subject when the wearable housing is worn by the subject, wherein the one or more transducers are coupled to the wearable housing such that the one or more transducers are spaced away at a distance from skin of the subject by a distance of at least about 1 millimeter. In some embodiments, the device further comprises one or more pressure sources configured to induce a pressure force onto one or more regions of the subject to generate the one or more auditory signals from said subject. In some embodiments, the one or more pressure sources comprise an air puff. In some embodiments, the one or more pressure sources comprise a mechanical actuator. In some embodiments, the one or more pressure sources comprise a voice coil, speaker, or any combination thereof. In some embodiments, the housing is a garment. In some embodiments, the housing is a rigid mechanical structure. In some embodiments, the one or more auditory signals comprise data capable of differentiating a healthy or an unhealthy state of the subject. In some embodiments, the one or more transducers are circular. In some embodiments, the device further comprises a processor in electrical communication with the one or more pressure sources, the one or more transducers, a control module, or any combination thereof. In some embodiments, the control module comprises a personal computer, cloud processing architecture, a personal mobile computing device, or any combination thereof.

In some aspects, the disclosure provided herein, in some embodiments, describes a system to determine a physiologic state of a subject, the system, in some embodiments comprises: a wearable housing; one or more transducers coupled to the wearable housing configured to receive one or more auditory signals from the subject when the wearable housing is worn by the subject, wherein the one or more transducers are coupled to the wearable housing such that the one or more transducers are spaced away from skin of the subject by a distance; and one or more processors configured to process the one or more auditory signals thereby determining the physiologic state of the subject. In some embodiments, the system further comprises one or more pressure sources configured to induce a pressure force onto one or more regions of the subject to generate the one or more auditory signals from the subject. In some embodiments, the one or more pressure sources comprise an air puff. In some embodiments, the one or more pressure sources comprise a mechanical actuator. In some embodiments, the one or more pressure sources comprise a voice coil, speaker, or any combination thereof. In some embodiments, the housing is a garment. In some embodiments, the housing is a rigid mechanical structure. In some embodiments, the one or more auditory signals comprise data capable of differentiating a healthy or an unhealthy state of the subject. In some embodiments, the one or more transducers are circular. In some embodiments, the system further comprises a control module in electrical communication with the one or more processor, the one or more pressure sources, the one or more transducers or any combination thereof. In some embodiments, the control module comprises a personal computer, cloud processing architecture, a personal mobile computing device, or any combination thereof. In some embodiments, the state is: healthy, chronic obstructive pulmonary disease, asthma, emphysema, pneumonia, congestive heart failure, any combination thereof states, or an indeterminant state.

In some aspects, the disclosure provided herein, in some embodiments, describes a method of determining a physiologic state of a subject, the method comprises: detecting one or more auditory signals from the subject using one or more air coupled auscultation modules; processing the one or more auditory signals to determine a correlative relationship between the one or more auditory signals from the subject and a library of one or more auditory signals; and determining the physiological state of the subject based on the correlative relationship between the one or more auditory signals. In some embodiments, the one or more air coupled auscultation modules comprise one or more transducers, one or more percussive elements, one or more processors, or any combination thereof. In some embodiments, the physiological state comprises a diseased state, wherein the diseased state comprises cancer, chronic obstructive pulmonary disease, emphysema, or any combination thereof. In some embodiments, the library comprises a correlative dataset correlating the subject's physiological state and a corresponding one or more auditory signals. In some embodiments, determining is accomplished by one or more machine learning algorithms. In some embodiments, the one or more machine learning algorithms comprise k-means clustering, neural network, random forest, Naïve bayes, support vector machine, decision tree, logistic regression, linear regression, or any combination thereof. In some embodiments, processing is completed in a cloud-based architecture, on-board within the one or more air coupled auscultation modules, on a remote computer server or any combination thereof. In some embodiments, determining is completed in a cloud-based architecture, on-board within the one or more air coupled auscultation modules, on a remote computer server or any combination thereof.

In some aspects, the disclosure provided herein, in some embodiments, describes a device to measure biological auditory signals, the device comprises: one or more transducers configured to receive one or more auditory signals from a subject, wherein the one or more transducers are not in contact with the subject.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings (also "Figure" and "FIG." herein), of which:

DETAILED DESCRIPTION

The present disclosure provides devices, systems, and methods configured to detect, analyze, or interpret one or more auditory signals generated by a subject. In some cases, the subject is a mammalian subject. In some instances, the mammalian subject is a human. In some cases, the one or more auditory signals may provide data or information to determine a physiological state of the subject. In some cases, the physiologic state of the subject may comprise a presence or lack thereof physiologic or anatomical changes of the subject that may be indicative of development of disease. In some cases, the disease may be cancer, chronic obstructive pulmonary disease, emphysema, asthma, acute respiratory distress syndrome, congestive heart failure, heart murmur, atrial fibrillation, blood clot, heart attack, vascular aneurysm, ventricular and/or atrial hypertrophy, or any combination thereof. In some instances, the detection of auditory signals may comprise the passive detection of auditory signals. In some cases, the auditory signals may be classified by anatomical or physiologic characteristics. For example, one or more auditory signals may be classified as lung wheezing, crackling, or other sounds indicative of a subject's lung function or the presence or lack thereof fluid in a subject's lungs.

In some cases, the devices, systems, and methods described herein may provide external physical force to determine mechanical properties of the subject. In some cases, the mechanical properties may comprise a presence or lack thereof fluid in the body of the subject, a change in tissue mechanical properties, or any combination thereof. In some cases, the change in tissue mechanical properties may be indicative of a change in physiologic or anatomical state of the subject.

In some cases, the systems may comprise one or more elements in electrical communication configured to detect auditory signals, process auditory signals, display information to a user of the system, receive input from a user of the system, or any combination thereof actions. In some instances, the user may be a medical doctor, nurse, nurse practitioner, or the subject themselves. In some cases, the information may comprise data and analytics regarding a physiologic state of the subject. The system may comprise one or more auscultation modules in electrical communication with elements of a control system configured to detect auditory signals from the subject. The system may comprise one or more pressure sources configured to apply pressure to the subject. In some instances, the system may comprise a control module in electrical communication with the one or more pressure sources and the one or more auscultation modules to detect auditory signals generated by the interaction of the subject and the pressure applied by the one or more pressure sources. Alternatively, or in combination, the control module may be in electrical communication with the one or more auscultation modules to detect one or more auditory signals of the subject without the generation of a pressure by the one or more pressure sources.

Auscultation Module

Figure 1A:
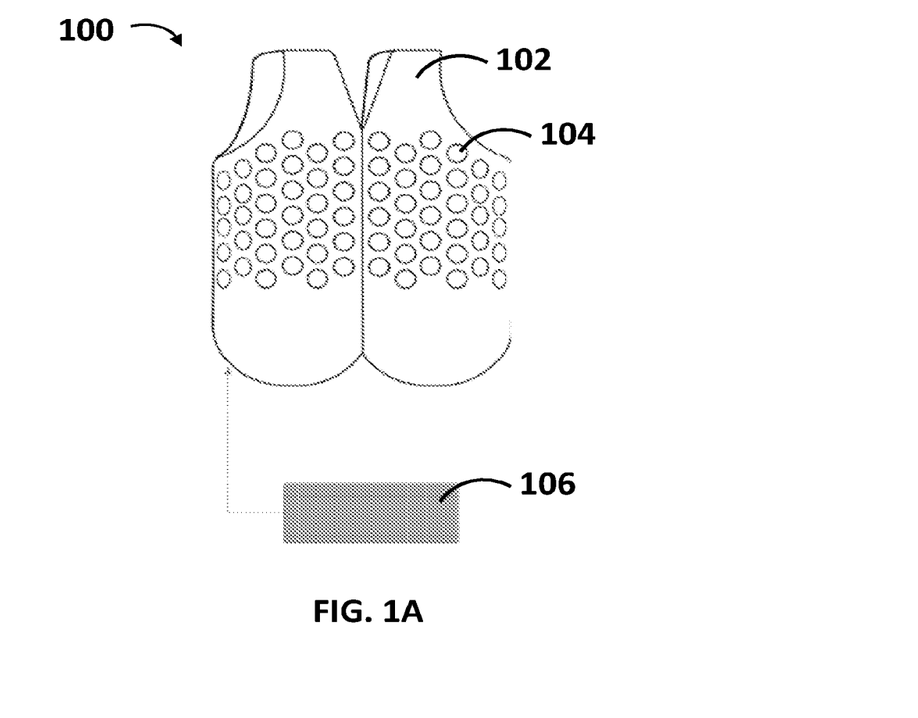
FIGS. 1A-1B illustrate a garment configured to house one or more auscultation modules (FIG. 1A) and show a detailed view of the auscultation module and internal components (FIG. 1B), as described in some embodiments herein.
Figure 1B:
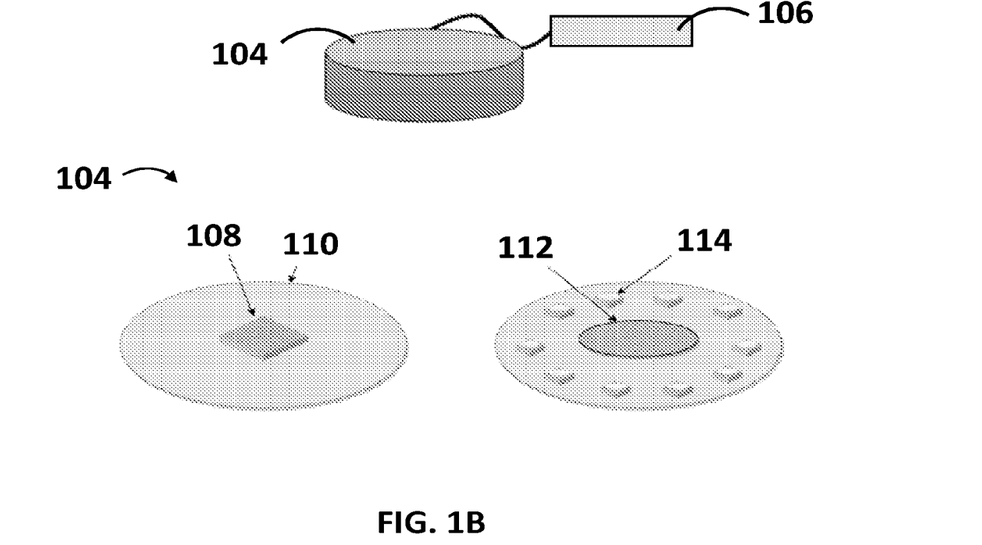

In some embodiments, the disclosure provided herein describes an auscultation module 104, as shown in FIGS. 1A-1B. One or more auscultation modules may be configured to detect auditory signals from a subject, described elsewhere herein. In some instances, the one or more auscultation modules may be positioned at a distance from the subject. In some cases, the one or more auscultation modules may not be in contact with the subject.

In some cases, one or more auscultation modules 104 may be mechanically coupled within a housing 102 configured to position the one or more auscultation modules with respect to a subject to measure auditory signals of the subject. In some cases, the housing may comprise a garment, as shown in FIG. 1A. In some instances, the garment may be worn underneath clothing of the subject. In some cases, the garment may cover the thorax of the subject. In some cases, the garment may be loose fitting on the subject. In some instances, the garment may provide access to areas of the subject's center thorax for cardio-thoracic procedures. In some cases, the cardio thoracic procedures may comprise repairing a pneumothorax, laparoscopic surgery, cardiac catherization, percutaneous coronary intervention, or any combination thereof procedure. In some cases, the garment may comprise antimicrobial properties. In some cases, the housing may comprise a wrist band or wrist strap. In some cases, the wrist band or wrist strap may wholly or partially encase or surround an arm or wrist of the subject. In some instances, the housing may comprise a rigid mechanical structure.

In some cases, the one or more auscultation modules may be in electrical communication with one or more power supplies 106. In some cases, the one or more power supplies may comprise one or more batteries. In some cases, the one or more batteries may be rechargeable. In some instances, the one or more power supplies may comprise an analog-current (AC) to direct-current (DC) converter that may convert the output of an electrical socket to power the one or more auscultation modules.

In some cases, the distance between the one or more auscultation modules and the subject may be about 1 mm to about 25 mm. In some cases, the distance between the one or more auscultation modules and the subject may be about 1 mm to about 2 mm, about 1 mm to about 3 mm, about 1 mm to about 4 mm, about 1 mm to about 5 mm, about 1 mm to about 8 mm, about 1 mm to about 10 mm, about 1 mm to about 12 mm, about 1 mm to about 14 mm, about 1 mm to about 16 mm, about 1 mm to about 18 mm, about 1 mm to about 25 mm, about 2 mm to about 3 mm, about 2 mm to about 4 mm, about 2 mm to about 5 mm, about 2 mm to about 8 mm, about 2 mm to about 10 mm, about 2 mm to about 12 mm, about 2 mm to about 14 mm, about 2 mm to about 16 mm, about 2 mm to about 18 mm, about 2 mm to about 25 mm, about 3 mm to about 4 mm, about 3 mm to about 5 mm, about 3 mm to about 8 mm, about 3 mm to about 10 mm, about 3 mm to about 12 mm, about 3 mm to about 14 mm, about 3 mm to about 16 mm, about 3 mm to about 18 mm, about 3 mm to about 25 mm, about 4 mm to about 5 mm, about 4 mm to about 8 mm, about 4 mm to about 10 mm, about 4 mm to about 12 mm, about 4 mm to about 14 mm, about 4 mm to about 16 mm, about 4 mm to about 18 mm, about 4 mm to about 25 mm, about 5 mm to about 8 mm, about 5 mm to about 10 mm, about 5 mm to about 12 mm, about 5 mm to about 14 mm, about 5 mm to about 16 mm, about 5 mm to about 18 mm, about 5 mm to about 25 mm, about 8 mm to about 10 mm, about 8 mm to about 12 mm, about 8 mm to about 14 mm, about 8 mm to about 16 mm, about 8 mm to about 18 mm, about 8 mm to about 25 mm, about 10 mm to about 12 mm, about 10 mm to about 14 mm, about 10 mm to about 16 mm, about 10 mm to about 18 mm, about 10 mm to about 25 mm, about 12 mm to about 14 mm, about 12 mm to about 16 mm, about 12 mm to about 18 mm, about 12 mm to about 25 mm, about 14 mm to about 16 mm, about 14 mm to about 18 mm, about 14 mm to about 25 mm, about 16 mm to about 18 mm, about 16 mm to about 25 mm, or about 18 mm to about 25 mm. In some cases, the distance between the one or more auscultation modules and the subject may be about 1 mm, about 2 mm, about 3 mm, about 4 mm, about 5 mm, about 8 mm, about 10 mm, about 12 mm, about 14 mm, about 16 mm, about 18 mm, or about 25 mm. In some cases, the distance between the one or more auscultation modules and the subject may be at least about 1 mm, about 2 mm, about 3 mm, about 4 mm, about 5 mm, about 8 mm, about 10 mm, about 12 mm, about 14 mm, about 16 mm, or about 18 mm. In some cases, the distance between the one or more auscultation modules and the subject may be at most about 2 mm, about 3 mm, about 4 mm, about 5 mm, about 8 mm, about 10 mm, about 12 mm, about 14 mm, about 16 mm, about 18 mm, or about 25 mm.

The auscultation module 104 may comprise: (a) one or more transducer elements 114 configured to detect acoustic and/or pressure waves of the auditory signals generated by the subject; (b) one or more pressure sources 112; (c) a processor 108 in electrical communication with the one or more transducer elements 114 and/or the one or more pressure sources 112. In some instances, the one or more transducer elements may be a micro-machined ultrasonic transducer, such as a capacitive micro-machined ultrasonic transducer (cMUT) or a piezoelectric micro-machined ultrasonic transducer (pMUT). Examples of cMUTs are provided in U.S. patent application Ser. No. 17/004,568, which is incorporated herein by reference. In some cases, the processor may be in electrical communication with one or more circuit elements. In some cases, the one or more circuit elements may comprise: a wireless (e.g., Bluetooth) transmitter and/or receiver, ultrasound digital signal processing (DSP) application specific integrated circuit, power regulator, a wireless (e.g., Bluetooth) transmitter and receiver antenna, or any combination thereof. In some cases, the auscultation module may comprise a heat dissipation structure, e.g., a heat sink.

In some cases, the one or more transducer elements 114 may comprise about 1 element to about 20 elements. In some cases, the one or more transducer elements 114 may comprise about 1 element to about 2 elements, about 1 element to about 4 elements, about 1 element to about 6 elements, about 1 element to about 8 elements, about 1 element to about 10 elements, about 1 element to about 12 elements, about 1 element to about 14 elements, about 1 element to about 16 elements, about 1 element to about 18 elements, about 1 element to about 20 elements, about 2 elements to about 4 elements, about 2 elements to about 6 elements, about 2 elements to about 8 elements, about 2 elements to about 10 elements, about 2 elements to about 12 elements, about 2 elements to about 14 elements, about 2 elements to about 16 elements, about 2 elements to about 18 elements, about 2 elements to about 20 elements, about 4 elements to about 6 elements, about 4 elements to about 8 elements, about 4 elements to about 10 elements, about 4 elements to about 12 elements, about 4 elements to about 14 elements, about 4 elements to about 16 elements, about 4 elements to about 18 elements, about 4 elements to about 20 elements, about 6 elements to about 8 elements, about 6 elements to about 10 elements, about 6 elements to about 12 elements, about 6 elements to about 14 elements, about 6 elements to about 16 elements, about 6 elements to about 18 elements, about 6 elements to about 20 elements, about 8 elements to about 10 elements, about 8 elements to about 12 elements, about 8 elements to about 14 elements, about 8 elements to about 16 elements, about 8 elements to about 18 elements, about 8 elements to about 20 elements, about 10 elements to about 12 elements, about 10 elements to about 14 elements, about 10 elements to about 16 elements, about 10 elements to about 18 elements, about 10 elements to about 20 elements, about 12 elements to about 14 elements, about 12 elements to about 16 elements, about 12 elements to about 18 elements, about 12 elements to about 20 elements, about 14 elements to about 16 elements, about 14 elements to about 18 elements, about 14 elements to about 20 elements, about 16 elements to about 18 elements, about 16 elements to about 20 elements, or about 18 elements to about 20 elements. In some cases, the one or more transducer elements 114 may comprise about 1 element, about 2 elements, about 4 elements, about 6 elements, about 8 elements, about 10 elements, about 12 elements, about 14 elements, about 16 elements, about 18 elements, or about 20 elements. In some cases, the one or more transducer elements 114 may comprise at least about 1 element, about 2 elements, about 4 elements, about 6 elements, about 8 elements, about 10 elements, about 12 elements, about 14 elements, about 16 elements, or about 18 elements. In some cases, the one or more transducer elements 114 may comprise at most about 2 elements, about 4 elements, about 6 elements, about 8 elements, about 10 elements, about 12 elements, about 14 elements, about 16 elements, about 18 elements, or about 20 elements.

In some cases, the processor may be configured to process detected auditory signals by the one or more transducer elements 114.

In some cases, the auscultation module 104 may comprise a circuitry 110 that may be a printed circuit board. In some cases, the processor 108, one or more circuit element, one or more transducer elements 114 and the one or more pressure sources 112 may be in electrical communication through the printed circuit board circuitry. In some cases, the printed circuit board may comprise at least 1 conductive layer, at least 2 conductive layers, at least 3 conductive layers, or at least 4 conductive layers. In some instances, the printed circuit board may comprise up to 1 conductive layer, up to 2 conductive layers, up to 3 conductive layers, or up to 4 conductive layers. In some cases, the one or more transducer elements 114 may be arranged in an array on the circuitry 110. In some cases, the one or more transducer elements 114 may be arranged in a circular array, linear array, polygonal array, or any combination thereof array.

In some cases, the auscultation module 104 may comprise one or more pressure sources 112 configured to generate pressure directed towards the subject. In some cases, the one or more pressure sources 112 may comprise a mechanical percussor, e.g., a spring-loaded CAM configured to transmit a mechanical vibration into the subject. In some cases, the one or more pressure sources 112 may comprise an acoustic percussor e.g., a magnetic voice coil, and/or speaker configured to transmit a low frequency pressure wave into the subject.

In some cases, the auscultation module 104 may be sealed wholly or partially within an enclosure. In some cases, the enclosure may comprise a plastic enclosure. In some cases, the auscultation module may comprise a circular, rectangular, square, triangular, trapezoidal, or any combination of shapes thereof. In some cases, the enclosure may provide one or more openings such that the one or more transducer elements 114 may receive and/or transmit auditory signals from the subject. In some instances, the enclosure may wholly or partially encase the one or more pressure sources such that the one or more pressure sources may be positioned in contact with the subject, yet the one or more transducer elements 114 may maintain a distance between the subject.

In some cases, the diameter of the enclosed auscultation module 104 may be about 5 mm to about 50 mm. In some cases, the diameter of the enclosed auscultation module 104 may be about 5 mm to about 10 mm, about 5 mm to about 15 mm, about 5 mm to about 20 mm, about 5 mm to about 25 mm, about 5 mm to about 30 mm, about 5 mm to about 35 mm, about 5 mm to about 40 mm, about 5 mm to about 45 mm, about 5 mm to about 50 mm, about 10 mm to about 15 mm, about 10 mm to about 20 mm, about 10 mm to about 25 mm, about 10 mm to about 30 mm, about 10 mm to about 35 mm, about 10 mm to about 40 mm, about 10 mm to about 45 mm, about 10 mm to about 50 mm, about 15 mm to about 20 mm, about 15 mm to about 25 mm, about 15 mm to about 30 mm, about 15 mm to about 35 mm, about 15 mm to about 40 mm, about 15 mm to about 45 mm, about 15 mm to about 50 mm, about 20 mm to about 25 mm, about 20 mm to about 30 mm, about 20 mm to about 35 mm, about 20 mm to about 40 mm, about 20 mm to about 45 mm, about 20 mm to about 50 mm, about 25 mm to about 30 mm, about 25 mm to about 35 mm, about 25 mm to about 40 mm, about 25 mm to about 45 mm, about 25 mm to about 50 mm, about 30 mm to about 35 mm, about 30 mm to about 40 mm, about 30 mm to about 45 mm, about 30 mm to about 50 mm, about 35 mm to about 40 mm, about 35 mm to about 45 mm, about 35 mm to about 50 mm, about 40 mm to about 45 mm, about 40 mm to about 50 mm, or about 45 mm to about 50 mm. In some cases, the diameter of the enclosed auscultation module 104 may be about 5 mm, about 10 mm, about 15 mm, about 20 mm, about 25 mm, about 30 mm, about 35 mm, about 40 mm, about 45 mm, or about 50 mm. In some cases, the diameter of the enclosed auscultation module 104 may be at least about 5 mm, about 10 mm, about 15 mm, about 20 mm, about 25 mm, about 30 mm, about 35 mm, about 40 mm, or about 45 mm. In some cases, the diameter of the enclosed auscultation module 104 may be at most about 10 mm, about 15 mm, about 20 mm, about 25 mm, about 30 mm, about 35 mm, about 40 mm, about 45 mm, or about 50 mm.

In some instances, the one or more transducer elements 114 may be configured to detect auditory signals from about 1 kHz to about 20 kHz. In some instances, the one or more transducer elements 114 may be configured to detect auditory signals from about 1 kHz to about 2 kHz, about 1 kHz to about 4 kHz, about 1 kHz to about 6 kHz, about 1 kHz to about 8 kHz, about 1 kHz to about 10 kHz, about 1 kHz to about 12 kHz, about 1 kHz to about 14 kHz, about 1 kHz to about 16 kHz, about 1 kHz to about 18 kHz, about 1 kHz to about 20 kHz, about 2 kHz to about 4 kHz, about 2 kHz to about 6 kHz, about 2 kHz to about 8 kHz, about 2 kHz to about 10 kHz, about 2 kHz to about 12 kHz, about 2 kHz to about 14 kHz, about 2 kHz to about 16 kHz, about 2 kHz to about 18 kHz, about 2 kHz to about 20 kHz, about 4 kHz to about 6 kHz, about 4 kHz to about 8 kHz, about 4 kHz to about 10 kHz, about 4 kHz to about 12 kHz, about 4 kHz to about 14 kHz, about 4 kHz to about 16 kHz, about 4 kHz to about 18 kHz, about 4 kHz to about 20 kHz, about 6 kHz to about 8 kHz, about 6 kHz to about 10 kHz, about 6 kHz to about 12 kHz, about 6 kHz to about 14 kHz, about 6 kHz to about 16 kHz, about 6 kHz to about 18 kHz, about 6 kHz to about 20 kHz, about 8 kHz to about 10 kHz, about 8 kHz to about 12 kHz, about 8 kHz to about 14 kHz, about 8 kHz to about 16 kHz, about 8 kHz to about 18 kHz, about 8 kHz to about 20 kHz, about 10 kHz to about 12 kHz, about 10 kHz to about 14 kHz, about 10 kHz to about 16 kHz, about 10 kHz to about 18 kHz, about 10 kHz to about 20 kHz, about 12 kHz to about 14 kHz, about 12 kHz to about 16 kHz, about 12 kHz to about 18 kHz, about 12 kHz to about 20 kHz, about 14 kHz to about 16 kHz, about 14 kHz to about 18 kHz, about 14 kHz to about 20 kHz, about 16 kHz to about 18 kHz, about 16 kHz to about 20 kHz, or about 18 kHz to about 20 kHz. In some instances, the one or more transducer elements 114 may be configured to detect auditory signals from about 1 kHz, about 2 kHz, about 4 kHz, about 6 kHz, about 8 kHz, about 10 kHz, about 12 kHz, about 14 kHz, about 16 kHz, about 18 kHz, or about 20 kHz. In some instances, the one or more transducer elements 114 may be configured to detect auditory signals from at least about 1 kHz, about 2 kHz, about 4 kHz, about 6 kHz, about 8 kHz, about 10 kHz, about 12 kHz, about 14 kHz, about 16 kHz, or about 18 kHz. In some instances, the one or more transducer elements 114 may be configured to detect auditory signals from at most about 2 kHz, about 4 kHz, about 6 kHz, about 8 kHz, about 10 kHz, about 12 kHz, about 14 kHz, about 16 kHz, about 18 kHz, or about 20 kHz.

Auscultation Systems

Figure 2:
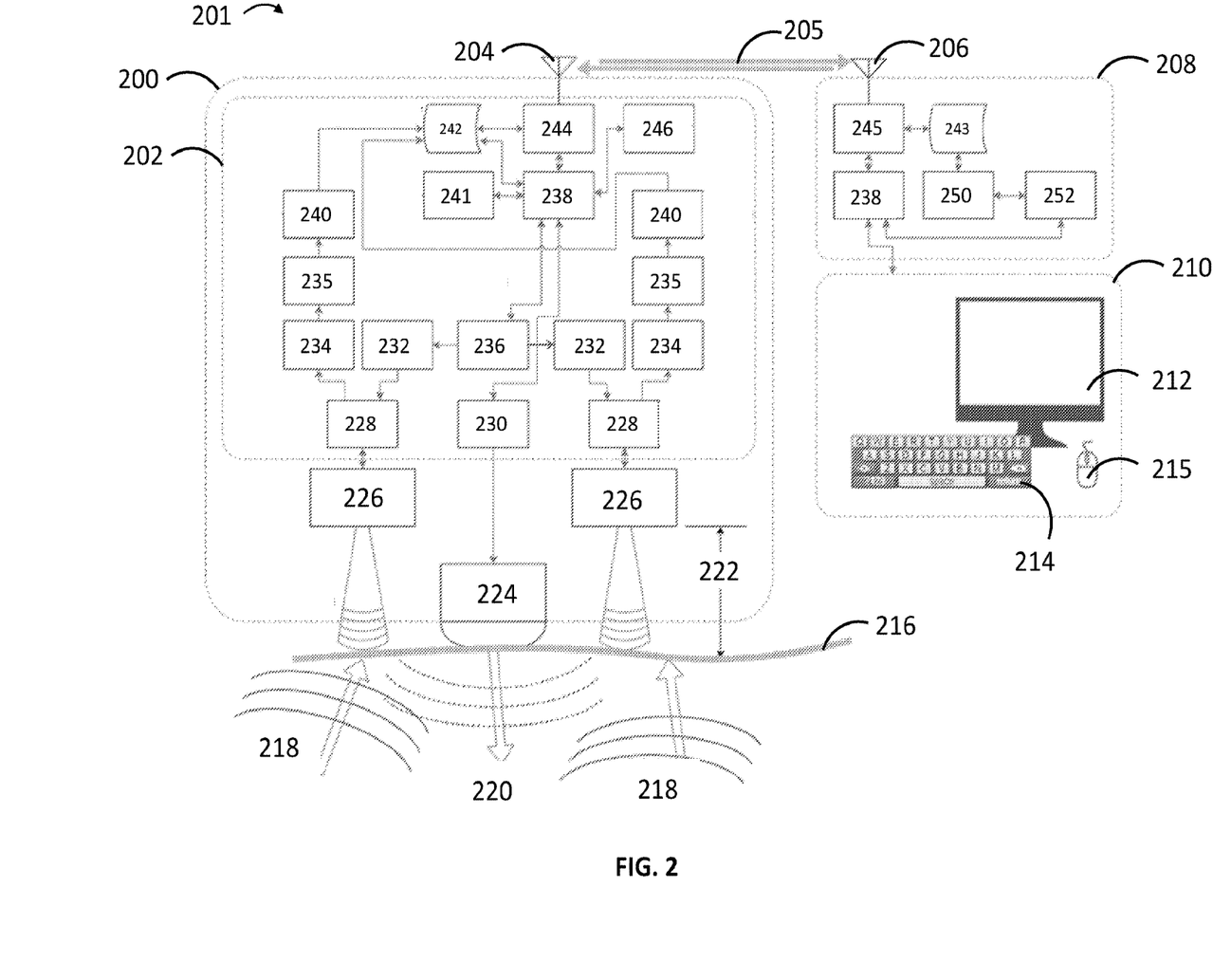
FIG. 2 illustrates a schematic diagram of the auscultation system disclosed herein, as described in some embodiments herein.

Aspects of the disclosure provided herein may comprise an auscultation system 201, as shown in FIG. 2, configured to detect auditory signals 218 and/or transmit auditory data of a subject to a control module 208 and/or a user interface 210. In some cases, the transmission of auditory data may be accomplished through a Bluetooth, WIFI, or any combination thereof transmission 205. In some cases, the system may comprise an auscultation module 200, described elsewhere herein. The auscultation module may be configured to detect auditory signals 218 from a surface 216 of the subject. The one or more auscultation modules may comprise a processing back end 202 that may comprise Bluetooth and/or WIFI data transmission and receiving 244 and/or ultrasound digital signal processing 240 integrated circuitry.

In some cases, the auscultation module 200 may comprise one or more ultrasound transducer elements 226, positioned at a distance 222 from a surface of the subject 216 configured to detect auditory signals 218 from the surface 216 of the subject. In some cases, the auditory signals 218 may be generated by the subject. In some cases, the auditory signals 218 may be generated by the interaction of one or more pressure sources (224,220) and the subject, described elsewhere herein.

In some cases, the processing back end 202 may comprise circuitry e.g., a clock 241, a central processing unit (CPU) 238, analog to digital converter 235, digital to analog converter 232, filter 234, transmit pulser 236, percussion controller 230, doppler detector 240, wireless data transmitter and receiver 244, accelerometer gyroscope integrated circuit 246, or any combination thereof configured to control system elements (e.g., one or more ultrasound transducer elements 226 and/or one or more pressure sources 224), transmit data, receive data, or any combination thereof.

In some cases, auditory signals 218 produced by the subject 216 may be detected by the one or more ultrasound transducer elements 226 in electrical communication with an ultrasound transmit/receive controller 228. In some instances, the transmit pulser 236 in electrical communication with the CPU 238 may generate one or more pulse signals that may be in electrical communication with the digital to analog converter 235. The one or more pulse signals transmitted to the digital to analog converter 235 may then be transmitted electrically to the ultrasound transducer element 226 to generate ultrasound signal directed to one or more regions of the subject. The ultrasound signal directed to the one or more regions of the subject 216 may then be used to detect motion of the one or more regions of the subject as a result of audio signals generated by the subject 218.

Alternatively or in combination, the CPU 238 may provide a driving signal to a percussion controller 230 configured to provide a driving signal for the one or more pressure sources 224, that may then produce auditory signals within the subject 216 that may be detected by the one or more ultrasound transducer elements 226. In some cases, the clock 241 of an auscultation module 200 may provide a common temporal signal to compare the detected auditory signals by the one or more ultrasound transducer elements 226 thereby determining a directionality or directional vector of an auditory signal wave front. In some cases, the clock 241 may provide a temporal clock signal to the transmit/receive controller 228 to sample the detected auditory signals with a known time interval. The detected auditory signal may then be filtered by the filter 234. In some cases, the filter 234 may comprise a bandpass, notch, low-pass, high-pass, or any combination thereof filter. After filtering the auditory signal, the signal may then be digitized by an analog to digital converter 235 and passed to a doppler detection circuit 240. In some cases, the doppler detection circuit 240 may convert the digitized data (i.e., the Doppler ultrasound data of surface displacement of the subject in units of distance) into a relative displacement. The relative displacement may then be converted into audio data. In some cases, the clock 241 may provide a temporal clock signal to the doppler detection circuit to sample the digitized analog auditory signal with a known time interval. The data may then be prepared into a data packet buffer 242 with discrete channels for each auscultation module 200 to determine the origin of the detected auditory signals. In some cases, simultaneous accelerometer and/or gyroscope data may be generated by the accelerometer gyroscope integrated circuit 246 and bundled by the CPU 238 with the digitized auditory signal data in the data packet buffer 242. In some cases, the accelerometer gyroscope integrated circuit 246 may measure spatial orientation (e.g., roll, pitch, yaw), angular orientation, acceleration, velocity, or any combination thereof data. In some instances, the data measured by the accelerometer gyroscope integrated circuit 246 may provide one or more spatial vectors to localize where within the subject the auditory signal originated.

After or during (e.g., asynchronously) acquisition and bundling of the channels of auditory signals into a data packet buffer 244, the system may then transmit data wirelessly to a control module 208 for further processing via the wireless data transmitter and receiver 244 in electrical communication with an antenna 204. In some cases, the wireless transmission may be Bluetooth transmission, WIFI transmission, or any combination thereof. The signal may then be detected by the control module 208 corresponding antenna 206 and wireless data transmitter and receiver 245.

The control module CPU 238 may then generate a clock signal 252 driving an analyzing circuit 250 to process all and/or a portion thereof the channels of auditory signals stored in the data packet buffer 243.

Alternatively, the channels of auditory signals may transmit via a wireless transmission system 244, 204 to be processed in a cloud-based processing architecture.

In some cases, the analyzing circuit 250 and/or cloud-based processing architecture may perform one or more processing operation to classify an auditory signal of the auditory signals. In some cases, the processing operation may comprise a cross-correlation, eigenvector-correlation, Ahn-park correlation, or any combination thereof. Alternatively or in combination, the processing operation may be a classification by a machine learning algorithm trained previously on a library of labeled auditory signals. In some embodiments, the machine learning algorithm may comprise a deep neural network (DNN). The deep neural network may comprise a convolutional neural network (CNN). The CNN may be, for example, U-Net, ImageNet, LeNet-5, AlexNet, ZFNet, GoogleNet, VGGNet, ResNet18 or ResNet, etc. Other neural networks may be, for example, deep feed forward neural network, recurrent neural network, LSTM (Long Short Term Memory), GRU (Gated Recurrent Unit), Auto Encoder, variational autoencoder, adversarial autoencoder, denoising auto encoder, sparse auto encoder, boltzmann machine, RBM (Restricted BM), deep belief network, generative adversarial network (GAN), deep residual network, capsule network, or attention/transformer networks, etc.

In some instances, the machine learning model may comprise clustering, scalar vector machines, kernel SVM, linear discriminant analysis, Quadratic discriminant analysis, neighborhood component analysis, manifold learning, convolutional neural networks, reinforcement learning, random forest, Naive Bayes, gaussian mixtures, Hidden Markov model, Monte Carlo, restrict Boltzmann machine, linear regression, or any combination thereof.

In some cases, the machine learning algorithm may include ensemble learning algorithms such as bagging, boosting and stacking. The machine learning algorithm may be individually applied to the plurality of features extracted for each channel, such that each channel may have a separate iteration of the machine learning algorithm or applied to the plurality of features extracted from all channels or a subset of channels at once.

In some cases, the classified channels of auditory signals and the spatial information for each channel determined by the accelerometer gyroscope integrated circuit 246 may be utilized to determine a 3-D spatial position of an auditory signal of a channel within a subject.

In some cases, the system may comprise a user interface 210 where a user may interact with, explore, or visualize raw auditory signal for each channel, the classified auditory signal, reconstructed spatial image of auditory signal classification, or any combination thereof signals. In some instances, the user interface 210 may display a 3-D spatial map and/or image of auditory signal classification overlaid over a model of a human torso for aid of visualization. In some cases, the CPU 238 may transmit the auditory signals to a user interface that may comprise a personal computer 212, laptop computer, smartphone, tablet, or any combination thereof. Alternatively or in combination, the cloud-based processing architecture may wirelessly transmit the channels of auditory signals to the user interface 210. In some cases, the user may interact with the auditory signals via a keyboard 214 and mouse 215. In some cases, a user, through the use of the user interface, may adjust or tune parameters of the auscultation system 201 (e.g., sensitivity and/or gain of the one or more ultrasound transducer elements 226, pressure force generated by the one or more pressure sources 224, the frequency of the pressure applied by the one or more pressure sources 224, etc, or any combination thereof) to improve signal-to-noise of the channels of detected auditory signals.

Methods

Figure 3:
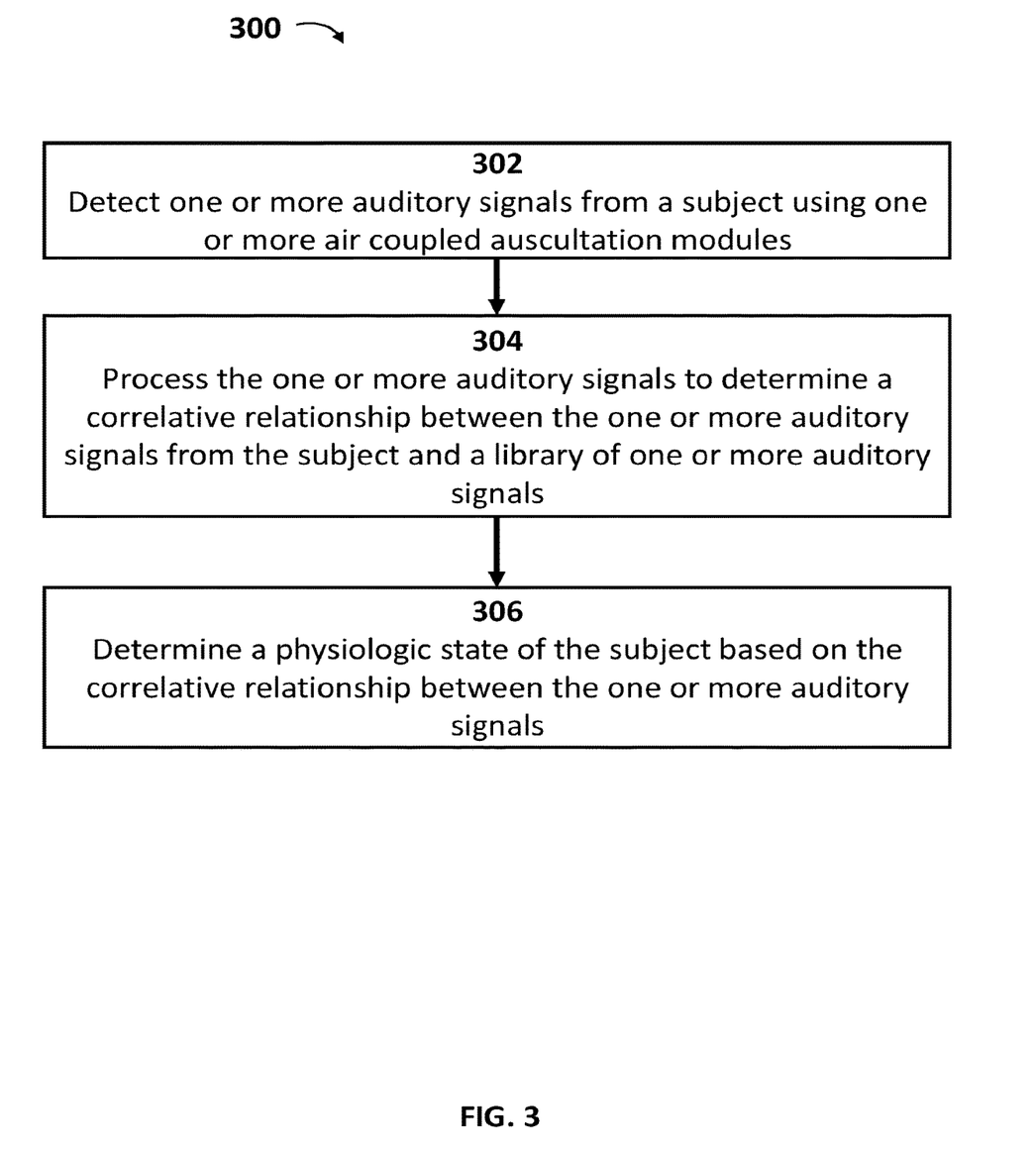
FIG. 3 illustrates a flow chart for a method of determining the physiologic state of a subject, as described in some embodiments herein.

Aspects of the disclosure provided herein may comprise a method 300 of determining a physiologic state of a subject, as seen in FIG. 3. In some cases, the method 300 may comprise the steps of: (a) detecting one or more auditory signals from a subject using one or more air coupled auscultation modules 302; (b) processing the one or more auditory signals to determine a correlative relationship between the one or more auditory signals from the subject and a library of one or more auditory signals 304; and (c) determining the physiologic state of the subject based on the correlative relationship between the one or more auditory signals 306. In some cases, the air coupled auscultation modules, described elsewhere herein, may comprise one or more transducers, one or more pressure sources, one or more processors, or any combination thereof.

In some cases, the physiologic state may comprise a vital. In some cases, the vital may comprise blood pressure, pulse, blood flow, hematocrit, or any combination thereof. In some cases, the physiologic state may comprise a diseased state. The diseased state may comprise cancer, chronic obstructive pulmonary disease, emphysema, asthma, acute respiratory distress syndrome, congestive heart failure, heart murmur, atrial fibrillation, blood clot, heart attack, vascular aneurysm, ventricular hypertrophy, pneumonia or any combination thereof. In some cases, the library may comprise a correlative dataset correlating a subject's physiological state and a corresponding one or more classified auditory signals. In some instances, the one or more classified auditory signals may be classified by an expert interpreter (e.g., medical personnel, resident physician, attending physician, respiratory therapist, nurse, etc.) In some cases, determining of step 306 may be accomplished by one or more machine learning algorithms, described elsewhere herein. In some instances, processing of step 304 may be completed in a cloud base architecture, on-board within the one or more air coupled auscultation modules, on a remote computer server, or any combination thereof. In some instances, determining of step 306 may be completed in a cloud-based architecture, on-board within the one or more air coupled auscultation modules, on a remote computer server, or any combination thereof.

In some cases, the disclosure provided herein may comprise a method of determining the spatial origin of auditory signals. In some cases, the method may comprise the steps of: (a) detecting one or more auditory signals from a subject using one or more air coupled auscultation modules; (b) determining a wave front orientation of the auditory signals from one or more ultrasound transducers within the one or more air coupled auscultation modules; and (c) comparing the spatial overlap of the wave front orientation of similar auditory signals thereby determining the spatial origin of the auditory signal. In some cases, the one or more auscultation modules may comprise Bluetooth transmission circuitry. In some cases, the Bluetooth transmission circuitry may be configured to communication between one or more auscultation modules to determine the relative angle and distances between the one or more auscultation modules. In some cases, the relative angle of a given auscultation module of the one or more auscultation modules may be determined by an accelerometer or gyroscopic circuit of the auscultation module. In some instances, the relative angle and distance between the one or more auscultation modules may be transmitted between the one or more auscultation modules via a Bluetooth antenna.

Although the above steps show each of the methods or sets of operations in accordance with embodiments, a person of ordinary skill in the art will recognize many variations based on the teaching described herein. The steps may be completed in a different order. Steps may be added or omitted. Some of the steps may comprise sub-steps. Many of the steps may be repeated as often as beneficial.

One or more of the steps of each method or sets of operations may be performed with circuitry as described herein, for example, one or more of the processor or logic circuitry such as programmable array logic for a field programmable gate array. The circuitry may be programmed to provide one or more of the steps of each of the methods or sets of operations and the program may comprise program instructions stored on a non-transitory computer readable memory or programmed steps of the logic circuitry such as the programmable array logic or the field programmable gate array, for example.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

Certain inventive embodiments herein contemplate numerical ranges. When ranges are present, the ranges include the range endpoints. Additionally, every sub range and value within the range is present as if explicitly written out. The term "about" or "approximately" may mean within an acceptable error range for the particular value, which will depend in part on how the value is measured or determined, e.g., the limitations of the measurement system. For example, "about" may mean within 1 or more than 1 standard deviation, per the practice in the art. Alternatively, "about" may mean a range of up to 20%, up to 10%, up to 5%, or up to 1% of a given value. Where particular values are described in the application and claims, unless otherwise stated the term "about" meaning within an acceptable error range for the particular value may be assumed.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A system to determine a physiologic state of a subject, the system comprising:
   (a) a wearable housing;
   (b) one or more auscultation modules coupled to said wearable housing and comprising:
      (i) one or more pressure sources configured to induce a pressure force onto one or more regions of a subject; and
      (ii) one or more ultrasound transducers configured to receive one or more ultrasound signals from said subject and generated in response to said pressure force when said wearable housing is worn by said subject, wherein said one or more ultrasound transducers are spaced away from a skin of said subject by a distance; and
   (c) one or more processors configured to process said one or more ultrasound signals received from said subject and form a measurement of one or more auditory signals from said subject, thereby determining said physiologic state of said subject.

2. The system of claim 1, wherein said one or more pressure sources comprise an air puff.

3. The system of claim 1, wherein said one or more pressure sources comprise a mechanical actuator.

4. The system of claim 1, wherein said one or more pressure sources comprise a voice coil, speaker, or any combination thereof.

5. The system of claim 1, wherein said wearable housing is a garment.

6. The system of claim 1, wherein said wearable housing is a rigid mechanical structure.

7. The system of claim 1, wherein said measurement of one or more auditory signals comprises data capable of differentiating a healthy state or an unhealthy state of said subject.

8. The system of claim 7, further comprising a clock in electrical communication with said one or more processors.

9. The system of claim 8, wherein said clock is configured to provide a common temporal signal to compare a detected said one or more auditory signals thereby determining a directionality or directional vector of an auditory signal wave of said one or more auditory signals.

10. The system of claim 1, wherein said one or more auscultation modules are circular.

11. The system of claim 1, further comprising a control module in electrical communication with said one or more processors, said one or more pressure sources, said one or more auscultation modules, or any combination thereof.

12. The system of claim 11, wherein said control module comprises a personal computer, a cloud processing architecture, a personal mobile computing device, or any combination thereof.

13. The system of claim 1, wherein said physiological state is: healthy, chronic obstructive pulmonary disease, asthma, emphysema, pneumonia, congestive heart failure, any combination thereof states, or an indeterminant state.

14. The system of claim 1, wherein said distance comprises a distance of at least about 1 millimeter.

15. The system of claim 1, wherein said one or more ultrasound transducers comprise a micro-machined ultrasonic transducer.

16. The system of claim 1, wherein said physiological state comprises a diseased state, and wherein said diseased state comprises cancer, chronic obstructive pulmonary disease, emphysema, or any combination thereof.

17. The system of claim 1, wherein said determining said physiologic state of said subject is accomplished by one or more machine learning algorithms.

18. The system of claim 17, wherein said one or more machine learning algorithms comprise k-means clustering, neural network, random forest, Naïve bayes, support vector machines, decision tree, logistic regression, linear regression, or any combination thereof.

19. The system of claim 1, wherein said processing is completed in a cloud-based architecture, on-board within said one or more processors, on a remote computer server, or any combination thereof.

20. The system of claim 1, further comprising an accelerometer, gyroscope, or a combination thereof.

21. The system of claim 20, wherein data measured by said accelerometer, gyroscope, or a combination thereof, provide one or more spatial vectors that localize a region within said subject where said one or more ultrasound signals originate.

22. The system of claim 1, wherein said one or more ultrasound transducers are configured to transmit an ultrasound signal.

23. The system of claim 22, wherein said one or more received ultrasound signals generated in response to said pressure force are reflected from said transmitted ultrasound signal.

24. The system of claim 23, wherein said one or more received ultrasound signals comprise a Doppler ultrasound signal.

25. The system of claim 24, wherein said one or more processors are configured to extract said one or more auditory signals from said Doppler ultrasound signal.

26. The system of claim 24, wherein said Doppler ultrasound signal comprises a displacement of a surface of said skin of said subject.

27. The system of claim 26, wherein said displacement of said surface of said skin is processed by said one or more processors into a relative displacement of said surface of said skin of said subject.

28. The system of claim 27, wherein said one or more processors convert said relative displacement of said surface of said skin of said subject into audio data.

29. The system of claim 26, wherein said one or more ultrasound transducers detect said one or more auditory signals from said surface of said skin of said subject.

30. The system of claim 29, wherein said one or more ultrasound transducers are configured to transmit said ultrasound signals; wherein, when said wearable housing is worn by said subject, said one or more ultrasound transducers transmit said ultrasound signals to said surface of said skin of said subject through an air medium; and wherein said one or more auditory signals from said surface of said skin of said subject are generated in response to said transmitted ultrasound signals and conveyed back to said one or more ultrasound transducers through said air medium.

31. The system of claim 1, wherein said physiologic state comprises a vital sign.

32. The system of claim 1, wherein said one or more processors determine a correlative relationship between said one or more received ultrasound signals and a library of one or more ultrasound signals.

* * * * *